United States Patent
Maeda (10) Patent No.: US 8,720,186 B2
(45) Date of Patent: May 13, 2014

(54) CONTROL APPARATUS FOR GAS SENSOR (75) Inventor: Seiji Maeda, Inazawa (JP)

(73) Assignee: NGK Spark Plug Co., Ltd., Aichi (JP)

( * ) Notice: Subject to any disclaimer, the term of this patent is extended or adjusted under 35 U.S.C. 154(b) by 199 days.

(21) Appl. No.: 13/305,285

(22) Filed: Nov. 28, 2011

(65) Prior Publication Data
US 2012/0131909 A1    May 31, 2012

(30) Foreign Application Priority Data

Nov. 29, 2010   (JP) ................................. 2010-265173

(51) Int. Cl.
*F01N 3/00*   (2006.01)

(52) U.S. Cl.
USPC ................... 60/277; 60/274; 60/276; 60/285; 73/23.31; 73/23.32; 204/408; 204/424

(58) Field of Classification Search
USPC ........ 60/274, 276, 277, 285; 73/23.31, 23.32; 204/408, 424
See application file for complete search history.

(56) References Cited

U.S. PATENT DOCUMENTS

| | | | |
|---|---|---|---|
| 5,781,878 A | 7/1998 | Mizoguchi et al. | |
| 6,073,083 A | 6/2000 | Schnaibel et al. | |
| 6,205,989 B1 | 3/2001 | Aoki | |
| 6,286,493 B1 | 9/2001 | Aoki | |
| 6,656,337 B2* | 12/2003 | Kurokawa et al. | 204/425 |
| 6,922,639 B2* | 7/2005 | Kawase et al. | 702/24 |
| 7,614,392 B2* | 11/2009 | Fukagai et al. | 123/688 |
| 7,980,121 B2* | 7/2011 | Matsuoka et al. | 73/114.69 |
| 8,354,016 B2* | 1/2013 | Kerns et al. | 205/784.5 |
| 8,393,316 B2* | 3/2013 | Kunihiro | 123/697 |
| 2011/0016949 A1 | 1/2011 | Sasaki | |

FOREIGN PATENT DOCUMENTS

| | | |
|---|---|---|
| DE | 19622625 A1 | 12/1996 |
| EP | 0961020 A2 | 12/1999 |
| EP | 1033486 A2 | 6/2000 |
| GB | 2317017 A | 3/1998 |
| JP | 2000-258387 A | 9/2000 |
| WO | 2009/102072 A1 | 8/2009 |

OTHER PUBLICATIONS

Extended European Search Report dated Mar. 8, 2012 issued by the European Patent Office in counterpart European Patent Application No. 11009438.

* cited by examiner

*Primary Examiner* — Binh Q Tran
(74) *Attorney, Agent, or Firm* — Sughrue Mion, PLLC (57) ABSTRACT

A control apparatus (100) for a gas sensor (10) which includes a cell (2) composed of a solid electrolyte body and a pair of electrodes provided thereon. The control apparatus includes voltage application means (70) for applying a single pulse voltage to the cell over a constant energization time T; first-output-value obtaining means 70 for obtaining a first output value Vri1 from the cell when a first time t1 shorter than the constant energization time has elapsed; second-output-value obtaining means (70) for obtaining a second output value Vri2 from the cell when a second time t2 shorter than the constant energization time but longer than the first time has elapsed; and deterioration-degree detection means 70 for detecting the degree of deterioration of the cell on the basis of a difference ΔVri between the second output value and the first output value.

12 Claims, 5 Drawing Sheets

AIR-FUEL RATIO OF GAS TO BE MEASURED

CONTROL APPARATUS FOR GAS SENSOR

BACKGROUND OF THE INVENTION

1. Field of the Invention

The present invention relates to a gas sensor control apparatus which is connected to a gas sensor including a cell for detecting the concentration of a gas to be measured, and which obtains the impedance of the cell to thereby detect the degree of deterioration of the cell.

2. Description of the Related Art

Examples of known gas sensors used for improving fuel consumption of an internal combustion engine of an automobile or the like or for combustion control of the engine include an air-fuel ratio sensor, and an oxygen sensor for detecting the oxygen concentration of exhaust gas. Also, since more rigorous exhaust gas regulations for automobiles demand a reduction in the amount of nitrogen oxides ($NO_X$) contained in exhaust gas, $NO_X$ sensors capable of directly measuring the concentration of $NO_X$ have been developed.

Each of these gas sensors includes a cell composed of a solid electrolyte body formed of zirconia or the like and having oxygen-ion conductivity, and a pair of electrodes formed on the surface thereof, and detects the concentration of a specific gas on the basis of the output from the cell.

As such a gas sensor, an oxygen sensor is known in which a measurement electrode exposed to a gas to be measured is formed on the outer surface of a solid electrolyte body, a reference electrode exposed to a reference gas is formed on the inner surface of the solid electrolyte body, and the oxygen concentration of the gas to be measured is detected on the basis of a difference between the oxygen concentration of the gas to be measured and that of the reference gas. Since the solid electrolyte body does not exhibit oxygen ion conductivity unless it is heated to its activation temperature or higher, the gas sensor is equipped with a heater. By supplying electric current to the heater to thereby heat the cell, the cell can be stably maintained at a temperature equal to or higher than the activation temperature, and quick activation of the cell becomes possible.

Since the impedance of the cell changes in accordance with the temperature of the cell, this impedance is periodically detected, and the amount of electric current supplied to the heater is controlled such that the impedance coincides with a target impedance, whereby the temperature of the cell is controlled. A signal for impedance detection is input to the cell, and the impedance is detected on the basis of an output (response signal) at that time.

However, there is a problem in that the cell deteriorates with time due to repeated use of the gas sensor, and the impedance thereof increases gradually. Even in the case where the cell is used under the same temperature condition, when the cell deteriorates, the impedance thereof becomes greater than that measured when the cell was new. Therefore, at the time of the temperature control, the deteriorated cell may be determined to still be cool and heated excessively, which may change the output characteristic of the gas sensor, and which may further accelerate deterioration of the gas sensor.

In view of the above-described problem, a technique has been developed of obtaining a high-frequency-side impedance and a low-frequency-side impedance by applying a plurality of AC voltages of different frequencies to a cell, adjusting a target temperature of the cell on the basis of the high-frequency-side impedance, and detecting a change in the characteristic of the cell on the basis of the low-frequency-side impedance (see Patent Document 1). Patent Document 1 describes that, of the two impedances of the cell, the low-frequency-side impedance, which shows the resistance of the electrode interface, increases significantly as a result of deterioration of the cell with time. Thus, the degree of deterioration can be detected and the target temperature of the cell can be adjusted on the basis of a change in impedance when an AC voltage containing a low-frequency component is applied to a new cell and a change in impedance when the AC voltage is applied to a deteriorated cell.

[Patent Document 1] Japanese Patent Application Laid-Open (kokai) No. 2000-258387 (FIG. 48)

PROBLEMS TO BE SOLVED BY THE INVENTION

However, when a change arises owing to a disturbance of a gas to be measured, such as the temperature of the gas to be measured around the cell or the concentration of a specific gas contained in the gas to be measured surrounding the cell (e.g., an air-fuel-ratio atmosphere of exhaust gas), the impedance of the cell also changes, which makes accurate measurement of the impedance of the cell difficult. Therefore, the accuracy in detecting the degree of deterioration of the cell may decrease accordingly. Particularly, in the case of a gas sensor in which a solid electrolyte body is formed into a tubular shape, a measurement electrode is provided on the outer surface of the solid electrolyte body, and a reference electrode is provided on the inner surface of the solid electrolyte body. Because the measurement electrode comes into contact with a gas to be measured, the gas sensor is more likely to be influenced by a disturbance of the gas to be measured, whereby the above-described problem becomes remarkable.

SUMMARY OF THE INVENTION

It is therefore an object of the present invention to provide a control apparatus for a gas sensor which can accurately detect the degree of deterioration of a cell by canceling or zeroing out the influence of disturbance imparted by a gas to be measured.

The above object of the present invention has been achieved by providing a control apparatus for a gas sensor which includes a cell composed of an oxygen-ion-conductive solid electrolyte body and a pair of electrodes provided thereon and which generates a sensor output corresponding to concentration of a specific gas, said control apparatus comprising voltage application means for applying a single pulse voltage to the cell over a constant energization time; first-output-value obtaining means for obtaining a first output value from the cell when a first time shorter than the constant energization time has elapsed after the start of application of the single pulse voltage; second-output-value obtaining means for obtaining a second output value from the cell when a second time shorter than the constant energization time but longer than the first time has elapsed after the start of application of the single pulse voltage; and deterioration-degree detection means for detecting the degree of deterioration of the cell on the basis of a difference between the second output value and the first output value.

When a change arises in disturbance by a gas to be measured, such as a change in the temperature of the gas to be measured around the cell and a change in the concentration of a specific gas contained in the gas to be measured surrounding the cell (e.g., the air-fuel ratio of exhaust gas), the impedance of the cell (solid electrolyte body) changes, and accurate measurement of the impedance of the cell may become difficult. That is, the impedance of the cell changes not only due to deterioration of the cell, but also due to disturbance imparted by the gas to be measured. When a single pulse voltage is applied to the cell, the first and second outputs of the cell change due to the disturbance imparted by the gas to be measured. However, when the difference between the first and second outputs is employed, the degree of deterioration of the cell can be accurately detected by cancelling the influence of the disturbance imparted by the gas to be measured.

Particularly, in the case of a gas sensor in which a solid electrolyte body is formed into a tubular shape, a measurement electrode is provided on the outer surface of the solid electrolyte body, and a reference electrode is provided on the inner surface of the solid electrolyte body. Because the measurement electrode comes into contact with a gas to be measured, the gas sensor is more likely to be influenced by disturbance imparted by the gas to be measured. In this case, the present invention effectively addresses the above described problems of the prior art.

In the above-described control apparatus for a gas sensor, preferably, the second time is longer than two times the first time.

Since the deterioration of the cell reflects on the difference between the second and first output values to an increasing degree with the elapse of time after application of the single pulse voltage to the cell, the difference increases accordingly, whereby the degree of deterioration of the cell can be detected more accurately.

In the above-described control apparatus for a gas sensor, preferably, the voltage application means again applies the single pulse voltage after a waiting time equal to or longer than 10 times the constant energization time has elapsed after the previous application of the single pulse voltage.

Upon application of the single pulse voltage, a charge is stored in the cell, and orientation of the solid electrolyte body occurs. However, since the next supply of the single pulse voltage is performed after the above-described waiting time has elapsed after application of the single pulse voltage has ended, the charge stored in the cell is eliminated, whereby the cell can be returned to a normal state.

In the above-described control apparatus for a gas sensor, preferably, the gas sensor is placed in a passage through which exhaust gas from an internal combustion engine flows; the control apparatus comprises determination means for determining an air-fuel ratio of the exhaust gas based on the sensor output; and the deterioration-degree detection means detects the degree of deterioration when the air-fuel ratio determined by the determination means is a specific air-fuel ratio.

The difference between the second and first output values has a peak at a certain air-fuel ratio (for example a lean region), and may greatly change and become unstable in certain air-fuel ratio regions in which the difference is not the peak. In order to overcome such a drawback, when the air-fuel ratio assumes a specific value (for example a rich region), the degree of deterioration is detected. Thus, a situation can be avoided where the degree of deterioration of the cell is detected when the air-fuel ratio is in an air-fuel ratio region in which the difference is unstable.

In the above-described control apparatus, preferably, the determination means determines, on the basis of the sensor output, whether the air-fuel ratio of the exhaust gas is on a rich side or a lean side; and the deterioration-degree detection means detects the degree of deterioration when the specific air-fuel ratio determined by the determination means is an air-fuel ratio on the rich side.

Particularly, when the air-fuel ratio of the gas to be measured is on the lean side, the above-described difference between the second and first output values has a peak. Therefore, this configuration avoids a situation where the degree of deterioration of the cell is detected in a lean region in which a change of the difference is unstable. Thus, the detection accuracy of the degree of deterioration can be improved.

In the above-described control apparatus, preferably, the gas sensor includes a heater for heating the cell; and the control apparatus further comprises heater control means for controlling the amount of electric current supplied to the heater such that the cell assumes a target impedance, and changing means for changing the target impedance on the basis of the degree of deterioration detected by the deterioration-degree detection means.

According to such a control apparatus for a gas sensor, it is possible to change the target impedance on the basis of the degree of deterioration of the cell and accurately heat the cell by means of heating by the heater without accelerating the deterioration of the cell, whereby the service life of the gas sensor can be extended.

EFFECT OF THE PRESENT INVENTION

According to the present invention, the influence of disturbance by a gas to be measured is cancelled, whereby the degree of deterioration of the cell can be detected accurately.

DESCRIPTION OF REFERENCE NUMERALS

Reference numerals used to identify various features in the drawings include the following:

2: cell
4: heater
10: gas sensor
20: output detection circuit
30: pulse generating circuit (voltage application means)
60: heater control circuit (heater control means)
70: microcomputer (first-output-value obtaining means, second-output-value obtaining means, voltage application means, deterioration-degree detection means, determination means, changing means)
100: gas sensor control apparatus
T: constant energization time
t1: first time
t2: second time
Vri1: first output value
Vri2: second output value
$\Delta Vri$: difference

DETAILED DESCRIPTION OF THE PREFERRED EMBODIMENTS

An embodiment of the present invention will next be described with reference to the drawings. However, the present invention should not be construed as being limited thereto.

Figure 1:
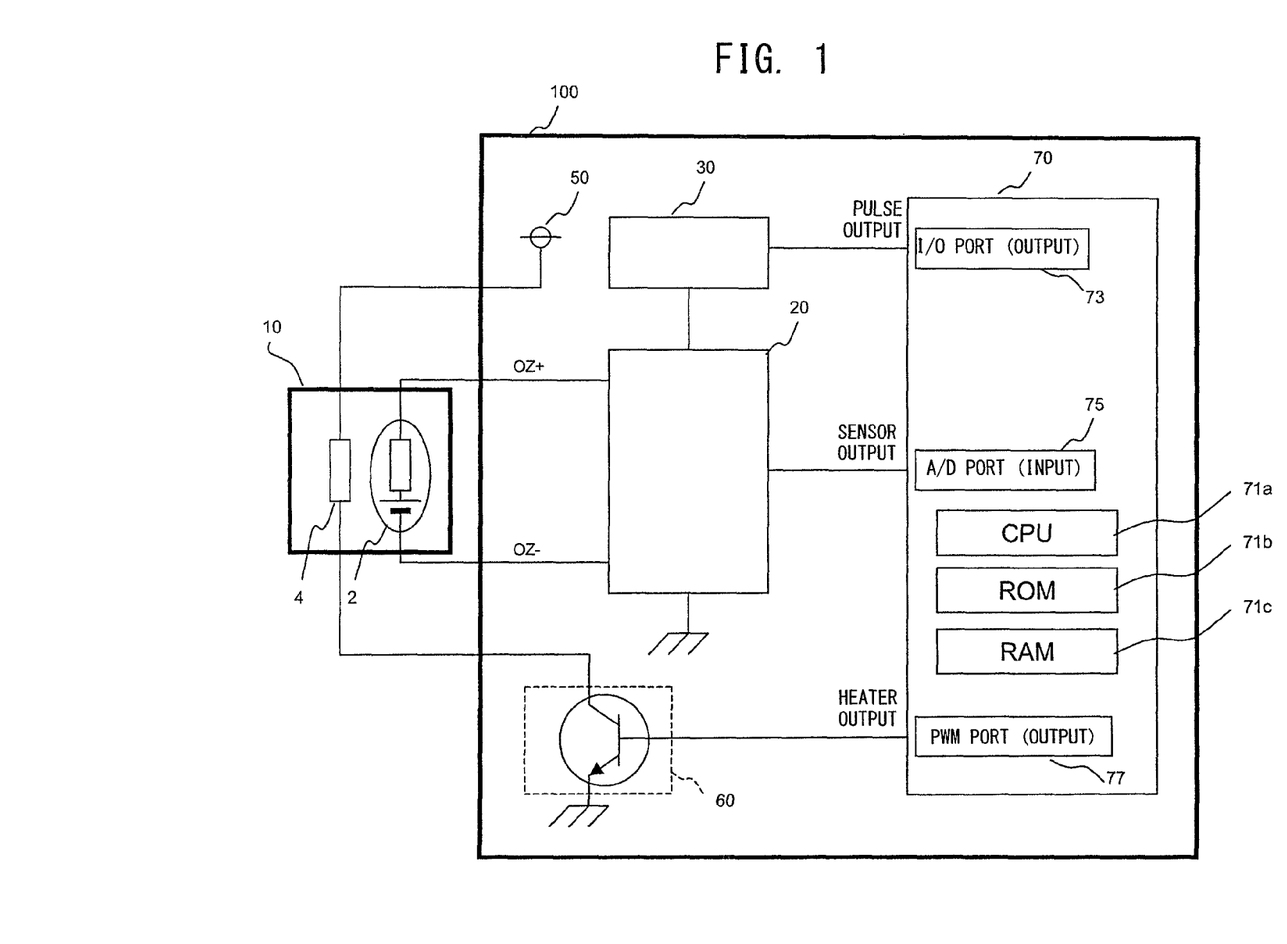
FIG. 1 is a schematic diagram showing the configuration of a control apparatus for a gas sensor.

FIG. 1 is a schematic diagram showing the configuration of a gas sensor control apparatus (ECU (Electronic Control Unit)) 100 according to the embodiment of the present invention. The ECU 100 is connected to a gas sensor 10, which is attached to an exhaust pipe of an engine. Notably, in the present embodiment, the present invention is applied to an example case where a flow path through which exhaust gas flows is the exhaust pipe. However, the present invention can be applied to a case where the gas sensor 10 is attached to a flow path which returns a portion of exhaust gas to an intake pipe where a gas mixture of new air and the returned exhaust gas is supplied to a combustion chamber. The gas sensor 10 includes a cell (detection element) 2 for detecting the concentration of oxygen contained in a gas to be measured (exhaust gas) and a heater 4 for maintaining the cell 2 at an operation temperature, and serves as a so-called λ (lambda) sensor for outputting an output signal corresponding to the air-fuel ratio of the exhaust gas.

The cell 2 includes an oxygen-ion-conductive solid electrolyte body having a bottomed tubular shape and formed of a partially stabilized zirconia ($ZrO_2$) or the like, and a pair of electrodes (a reference electrode and a detection electrode) (neither of which is shown) provided on the solid electrolyte body. Each electrode is mainly formed of, for example, platinum. An electromotive force is generated in accordance with a difference in oxygen concentration between the reference electrode, which is formed on the inner surface of the solid electrolyte body and exposed to a reference gas (specifically, atmospheric air), and the detection electrode formed on the outer surface of the solid electrolyte body and exposed to a gas to be measured. The concentration of oxygen (accordingly, the air-fuel ratio) can be measured by detecting the electromotive force.

Meanwhile, the heater 4 includes a heater wiring line (not shown) mainly formed of platinum and embedded in an alumina layer. The heater 4 is disposed inside the cell 2 (specifically, disposed in the interior space of the solid electrolyte body having a bottomed tubular shape). The heater 4 is controlled by electric power supplied from a heater control circuit 60 such that the temperature of the cell 2 becomes equal to a target activation temperature (in this embodiment, 830° C.). One end of the heater wiring line is electrically connected to the heater control circuit 60, and the other end of the heater wiring line is electrically connected to a battery 50 (in the present embodiment, a 12 V battery). As a result of heating by the heater 4, the cell 2 is activated, and detection of oxygen concentration (detection of air-fuel ratio) quickly becomes possible.

The ECU 100 includes an output detection circuit 20 for detecting a sensor output from the gas sensor 10 (the cell 2); a pulse generating circuit (corresponding to the "voltage application means" of the invention) 30; the heater control circuit 60 for controlling the heater 4; and a microcomputer 70 for controlling the entire ECU 100. The microcomputer 70 (corresponding to the "first-output-value obtaining means," the "second-output-value obtaining means," the "voltage application means," the "deterioration-degree detection means," the "determination means," and the "changing means" of the invention) is connected to the heater control circuit 60, and controls the heater control circuit 60 such that the temperature of the cell 2 coincides with an operation temperature (hereinafter, also referred to as an "activation temperature"). Also, the microcomputer 70 is connected to the output detection circuit 20 and the pulse generating circuit 30.

The output detection circuit 20 is a circuit which detects the sensor output (in the present embodiment, electromotive force) from the cell 2 and impedance signals Vri1 and Vri2 used for detecting the degree of deterioration of the cell 2, and which has a known circuit configuration using resistors, etc. Notably, the impedance signals Vri1 and Vri2 obtained via the output detection circuit 20 and the microcomputer 70 correspond to the "first output value" and the "second output value," respectively, of the invention.

The output detection circuit 20 outputs the detected sensor signals and the impedance signals Vri1 and Vri2 to the microcomputer 70 (an A/D port 75 thereof).

As a result of repeated use of the gas sensor 10, the cell 2 deteriorates with time and the impedance of the cell 2 changes accordingly. In view of this, in the present embodiment, a change in impedance caused by deterioration of the cell 2 (the state of impedance) is estimated by calculating a difference $\Delta Vri=|Vri2-Vri1|$ between the impedance signals Vri1 and Vri2 (corresponding to the "difference between the second output value and the first output value" of the invention).

The microcomputer 70 can be configured by a known microcomputer which includes a CPU (central processing unit) 71a, a storage section (RAM 71c and ROM 71b) for storing data and programs, and input/output ports 73, 75, and 77 which exchange signals with external equipment. The microcomputer 70 causes the CPU 71a to execute various types of computational processing on the basis of the programs stored in the storage section, and controls execution of instructions for computation, data transfer, etc. Also, the microcomputer 70 changes the contents of a input port register so as to reflect the signals input to the input port (the A/D port 75), and outputs the contents of a output port register as signals to the output ports (the I/O port 73 and the PWM (pulse-width-modulation) port 77).

The microcomputer 70 computes an oxygen concentration and then an air-fuel ratio on the basis of a sensor output (electromotive force) obtained via the output detection circuit 20. The microcomputer 70 determines whether the air-fuel ratio is on the rich side or the lean side, and executes combustion control, etc., for the engine, to thereby control the operation state of the engine.

Also, the microcomputer 70 converts the impedance signal Vri1 obtained via the output detection circuit 20 to a digital signal by use of an unillustrated A/D conversion circuit, calculates an impedance Ri of the cell 2 corresponding to Vri1 on the basis of the stored map or a calculation formula, and outputs an instruction for energizing the heater 4 to the heater control circuit 60 in accordance with the impedance Ri, to thereby execute heater energization control processing.

Moreover, the microcomputer 70 calculates the difference $\Delta Vri$ on the basis of the impedance signals Vri1 and Vri2 obtained via the output detection circuit 20, and detects the degree of deterioration of the cell 2 as described below.

The heater control circuit 60 includes a transistor. The collector of the transistor is connected to one end of the heater 4, the emitter thereof is grounded via a predetermined resistor, and the base thereof is connected to the microcomputer 70. Therefore, in a period during which the microcomputer 70 outputs to the base of the transistor a voltage level signal for turning the transistor on, a voltage is output from the battery 50 to the heater 4, whereby the heater 4 generates heat. Meanwhile, when the microcomputer 70 stops outputting the heater signal, the transistor enters an off state whereby heating by the heater 4 is stopped. More particularly, the microcomputer 70 outputs the heater signal, which is determined from a duty factor, to the heater control circuit 60 from the PWM port 77. Further, the heater control circuit 60 turns on and off in accordance with the heater signal, whereby the amount of electric current supplied to the heater 4 is controlled through PWM control. Notably, this heater control circuit 60, together with the microcomputer 70, constitutes the "heater control means" of the invention. The heater control circuit 60 is not limited to those constituted by transistors, and may be formed by use of an FET or the like.

Figure 2:
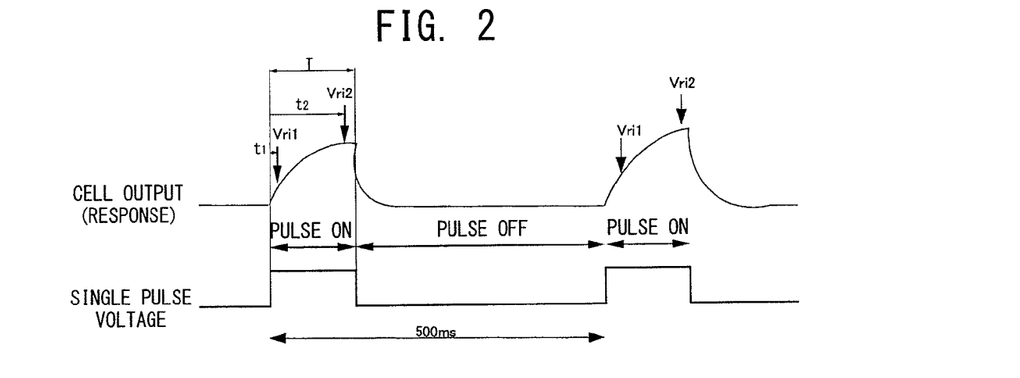
FIG. 2 is a chart showing the waveform of a single pulse voltage, and a method of detecting first and second output values (Vri1, Vri2) of a cell.

Next, with reference to FIG. 2, the waveform of a detection signal (corresponding to a "single pulse voltage" of the invention) for detecting the impedance signals Vri1 and Vri2, and a method for detecting the impedance signals will be described. Notably, the horizontal axis of FIG. 2 represents time, and the vertical axis thereof represents voltage.

First, the single pulse voltage has a rectangular waveform and is applied to the cell 2 over a fixed or constant energization time (pulse ON time) T. Specifically, digital data calculated by the microcomputer 70 are output (pulse output) from the I/O port 73 to the pulse generating circuit 30. Thus, the pulse generating circuit 30 applies the single pulse voltage having a rectangular waveform to the cell 2 via the output detection circuit 20. Notably, in the present embodiment, the total of the pulse ON time and the pulse OFF time is set to 500 ms.

The microcomputer 70 acquires a voltage Vri1 between the electrodes of the cell 2 via the output detection circuit 20 when a first time t1 shorter than the time T has elapsed after the start of application of the single pulse voltage. Subsequently, the microcomputer 70 acquires a voltage Vri2 between the electrodes of the cell 2 in the same manner when a second time t2 shorter than the time T but longer than the first time t1 has elapsed after the start of application of the single pulse voltage.

Since a change in the voltage between the electrodes of the cell 2 upon application of the single pulse voltage reflects a change in the impedance of the cell 2, the state of the impedance of the cell 2 and thus the degree of deterioration of the cell 2 can be detected by making use of Vri1 and Vri2 as impedance signals each representing the impedance of the cell 2.

Figure 3:
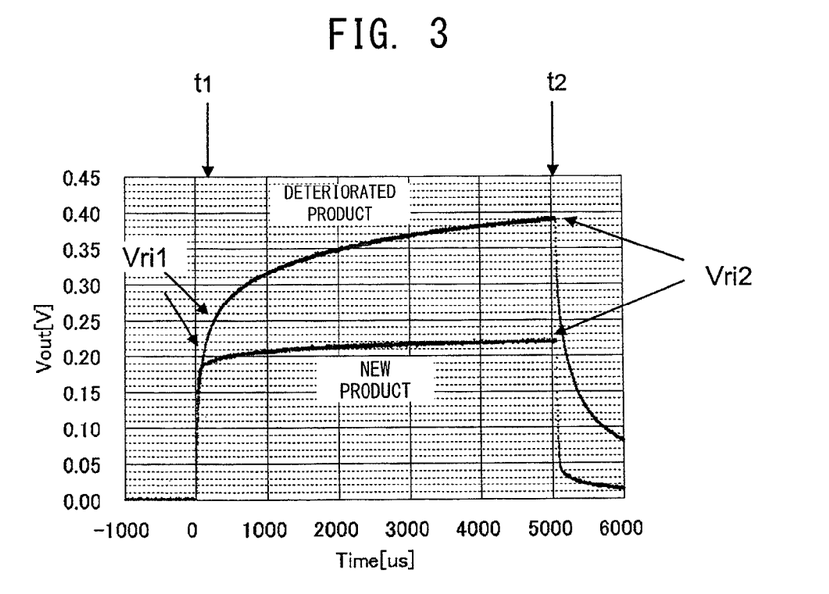
FIG. 3 is a chart showing actual measurement values of the first and second output values (Vri1, Vri2) obtained at first and second times, respectively.

FIG. 3 shows actual measurement values of the impedance signals Vri1 and Vri2 obtained upon elapse of the first time t1 and the second time t2, respectively. In FIG. 3, whereas a large increase from Vri1 to Vri2 is observed in the case of a deteriorated gas sensor (a gas sensor 10 used in travel of 60,000 km in total), only a slight increase from Vri1 to Vri2 is observed in the case of a new gas sensor 10 (that is, when the cell 2 is new). Accordingly, a change in the impedance of the cell 2 with time (the degree of deterioration of the cell 2) can be detected by calculating the difference ΔVri.

Figure 4:
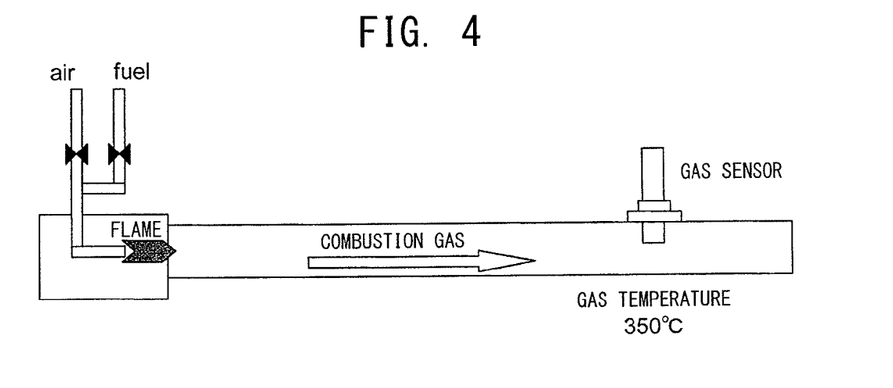
FIG. 4 is a view showing an experiment apparatus used for measuring the actual measurement values of FIG. 3.

Notably, the impedance signals Vri1 and Vri2 of FIG. 3 were measured by use of a single-tube burner shown in FIG. 4, in which an air-fuel mixture having an air-fuel ratio determined such that λ=0.95 was burned at one end of the burner, and the gas sensor 10 was attached to the single-tube burner at a position where the temperature of combustion gas became 350° C.

Here, the reason will be described for measuring the impedance signals Vri1 and Vri2 upon elapse of the first time t1 and the second time t2, respectively, after the start of supply of the single pulse voltage to the cell 2.

The present inventor has carried out various investigations and has found that, when changes arise in disturbance imparted by a gas to be measured, such as the temperature of the gas to be measured around the cell 2 and the concentration of a specific gas contained in the gas to be measured surrounding the cell 2 (the air-fuel ratio of exhaust gas), the impedance of the cell 2 changes. As a result, accurate measurement of the impedance of the cell 2 becomes difficult. That is, the impedance of the cell 2 changes not only due to deterioration of the cell 2 but also due to disturbance imparted by the gas to be measured.

Meanwhile, when a single pulse voltage is applied to the cell 2, the impedance signals Vri1 and Vri2 obtained from the cell 2 change due to the disturbance imparted by the gas to be measured. Accordingly, when the difference ΔVri between Vri1 and Vri2 is employed, the degree of deterioration of the cell 2 can be accurately detected by cancelling the influences of the disturbance imparted by the gas to be measured.

Notably, the deterioration of the cell 2 (if any) tends to be reflected in the difference ΔVri to an increasing degree as time has elapsed after the start of application of the single pulse voltage to the cell 2 (see the above-described FIG. 3). Therefore, the greater the difference between the first time t1 and the second time t2, the greater the value of ΔVri and the greater the degree to which deterioration of the cell is reflected in the difference between the second and first output values. In view of the above, preferably, the second time t2 is made longer than two times the first time t1. Although no particular limitation is imposed on the upper limit of the second time t2, the second time t2 is desirably made equal to or less than 200 times the first time t1.

Next, an algorism (flowchart) for detecting the degree of deterioration of the cell 2 will be described with reference to FIGS. 5A and 5B. Notably, in the present embodiment, the microcomputer 70 performs heater control (Ri constant control) in the main routine, and executes processing of detecting the degree of deterioration of the cell 2 in a subroutine called from the main routine. The processing interval of the Ri constant control is variable, and the Ri constant control processing is executed at intervals of a few hundreds ms to a few sec. The Ri constant control processing is performed by known PI (proportional-integral) computation. Specifically, a heater application voltage (effective voltage) for maintaining the gas sensor 10 at a constant temperature is calculated from the difference ΔRi between a target Ri ("target Ri" in FIGS. 5A and 5B) and Ri (actual measurement value) calculated from the impedance signal Vri1 obtained in step S8, described below. The supply of electric current to the heater 4 is controlled (through PWM control) via the heater control circuit 60 on the basis of this calculated heater application voltage.

Also, in synchronism with the start of the Ri constant control processing, the microcomputer 70 separately executes processing of detecting the temperature of the gas sensor 10. Although this temperature detection processing is well known, this processing will be described briefly. The microcomputer 70 obtains the impedance signal Vri1 from the output detection circuit 20 at a predetermined detection timing. Subsequently, the microcomputer 70 calculates the impedance Ri of the cell 2 by making use of a predetermined calculation formula or data (e.g., a two-dimensional map) representing the correlation between the impedance signal Vri1 and the impedance Ri of the cell 2. Subsequently, the microcomputer 70 performs the above-described Ri constant control processing on the basis of the calculated impedance Ri.

Figure 5A:
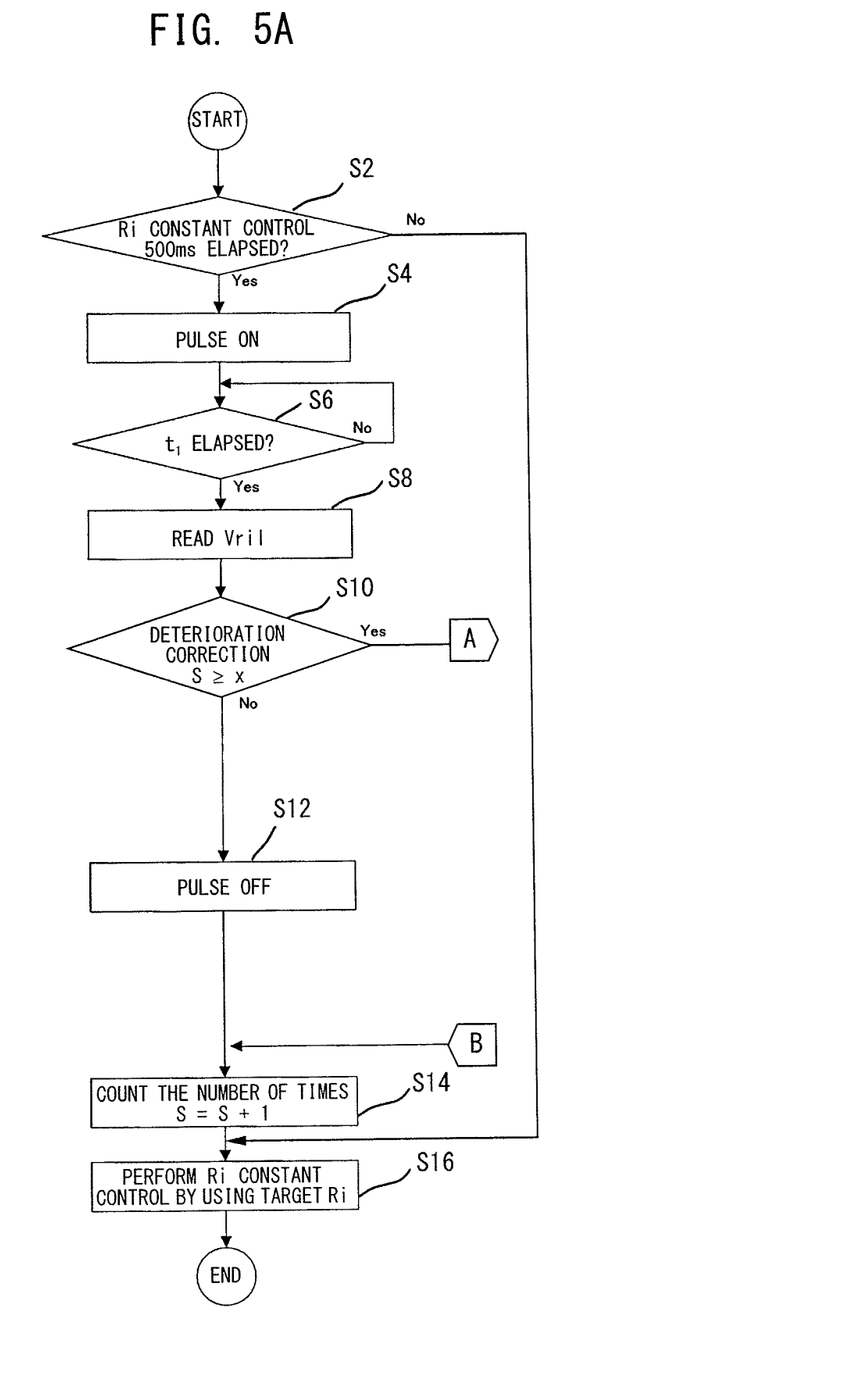
FIGS. 5A and 5B are flowcharts for detecting the degree of deterioration of the cell.
Figure 5B:
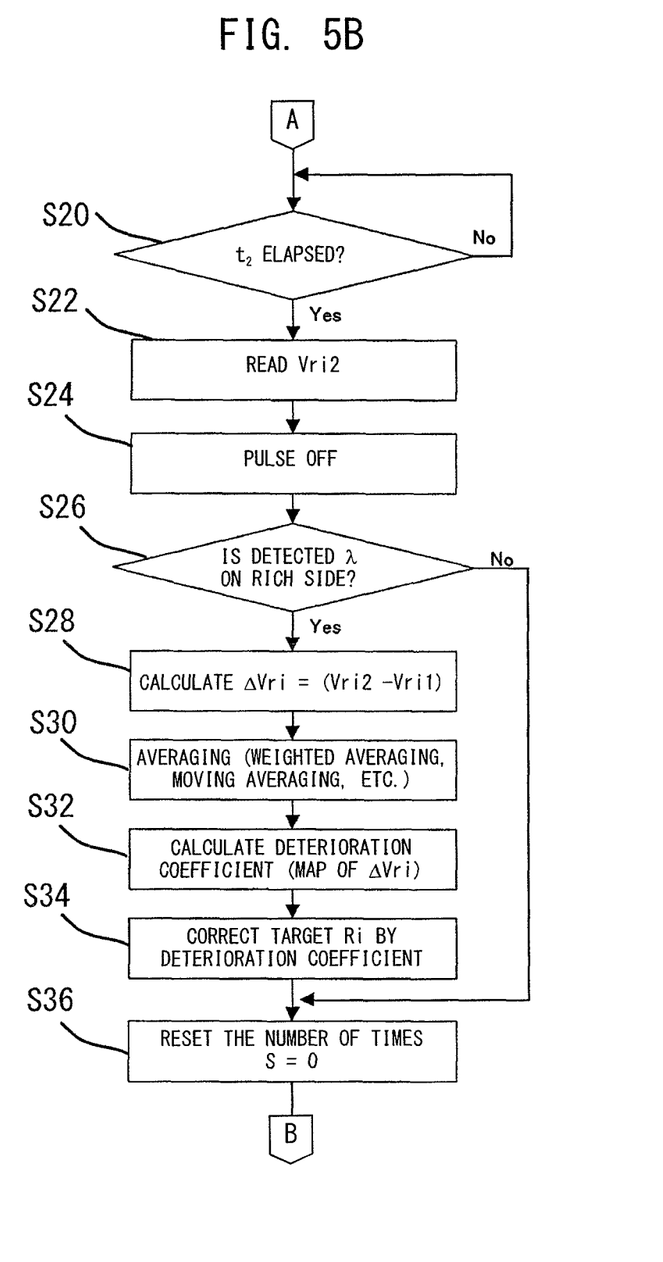

As shown in FIGS. 5A and 5B, the microcomputer 70 determines whether or not a predetermined time (500 ms) has elapsed after start of the Ri constant control processing (main routine) (step S2). In the case where the result of the determination in step S2 is "Yes", the microcomputer 70 outputs the above-described pulse output to the pulse generating circuit 30 (step S4). As a result, a single pulse voltage is applied to the cell 2 (pulse ON). Meanwhile, in the case where the result of the determination in step S2 is "No", the microcomputer 70 proceeds to step S16. In step S16, the microcomputer 70 compares the actual impedance and the target Ri corrected in S34, to thereby perform the heater control (Ri constant control) processing. After step S16, the microcomputer 70 ends the processing of detecting the degree of deterioration of the cell 2, and returns to the main routine.

Subsequent to step S4, the microcomputer 70 determines whether or not the first time t1 has elapsed after the pulse ON (step S6). In the case where the result of the determination in step S6 is "Yes", the microcomputer 70 obtains (reads) the impedance signal Vri1 via the output detection circuit 20 (step S8). Meanwhile, in the case where the result of the determination in step S6 is "No", the microcomputer 70 repeats the processing of step S6 until the first time t1 has elapsed.

Subsequent to step S8, through a comparison between an integer s and a deterioration detection timing coefficient x, the microcomputer 70 determines whether or not deterioration detection processing is to be performed (step S10). The deterioration detection timing coefficient x is a constant equal to or greater than 1, and the integer s is a variable whose initial value is equal to or greater than 1 and which is stored in the microcomputer 70. In the case where the result of the determination in step S10 is "Yes" (s≥x), the microcomputer 70 proceeds to step S20.

Figure 6A:
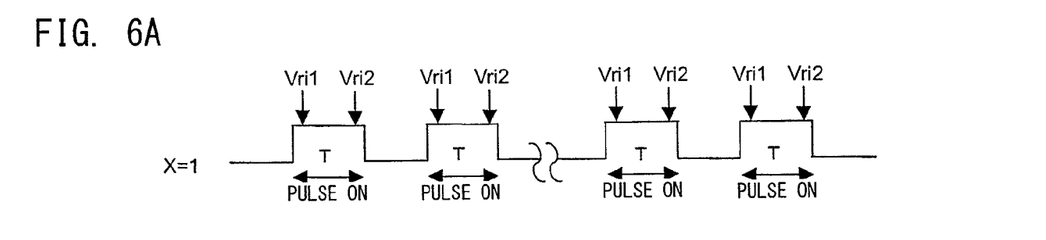
FIGS. 6A and 6B are charts showing the waveform of a single pulse voltage and timings for obtaining the first and second output values of the cell, for the case where a deterioration detection timing coefficient x=1 or 10.

Notably, as a result of the increment processing of step S14, the integer s always becomes 1 or greater. Therefore, in the case where the deterioration detection timing coefficient x is set to 1, the microcomputer 70 always makes a "Yes" determination in step S10. For example, a the waveform of the single pulse voltage of FIG. 2 shows the case where x=1. That is, in the case where x=1, as shown in FIG. 6A, the pulse width of the single pulse voltage is always equal to the constant energization time T. Both the impedance signals Vri1 and Vri2 are obtained during each period during which a pulse is ON, the difference ΔVri is calculated for each period or pulse, and the impedance Ri of the cell 2 and the degree of deterioration thereof are detected for each period or pulse.

Specifically, in the case where the result of the determination in step S10 of FIG. 5A is "Yes", the microcomputer 70 determines whether or not the second time t2 has elapsed after the pulse ON (step S20). In the case where the result of the determination in step S20 is "Yes", the microcomputer 70 obtains (reads) the impedance signal Vri2 via the output detection circuit 20 (step S22). Meanwhile, in the case where the result of the determination in step S20 is "No", the microcomputer 70 repeats the processing of step S20 until the second time t2 has elapsed.

Subsequent to step S22, the microcomputer 70 stops output of the pulse output to the pulse generating circuit 30 to thereby stop application of the single pulse voltage to the cell 2 (pulse OFF) (step S24). As a result, the pulse width of the single pulse voltage becomes equal to the constant energization time T. Subsequent to step S24, the microcomputer 70 computes the air-fuel ratio (λ) of exhaust gas on the basis of the sensor output acquired via the output detection circuit 20, and determines whether or not the air-fuel ratio (λ) is on the rich side (step S26).

In the case where the result of the determination in step S26 is "Yes", the microcomputer 70 calculates the difference ΔVri=|Vri2−Vri1| (step S28). The microcomputer 70 performs averaging of the difference ΔVri (step S30), and then calculates a deterioration constant (corresponding to the "degree of deterioration" of the invention) of the cell 2 on the basis of the difference ΔVri (step S32). Next, the microcomputer 70 corrects the target Ri on the basis of the deterioration constant (step S34). As a result, the target Ri which is determined in consideration of the degree of deterioration of the cell 2 is set.

Notably, the averaging of the difference ΔVri is performed as follows. A plurality of the difference ΔVri values obtained within a predetermined time (for example, 10 ΔVri values obtained in periods corresponding to s=1 to 10 of FIG. 6A (FIG. 6A shows only four of the 10 values) are averaged (moving average). The method of averaging is not limited to the above-described moving average, and, for example, a weighted average or the like may be used.

The calculation of the deterioration constant of the cell 2 may be performed by making use of a predetermined calculation formula or data (e.g., a two-dimensional map) representing the correlation between the difference ΔVri (the averaging of the difference ΔVri) and the deterioration constant.

Subsequent to step S34, the microcomputer 70 resets the integer s to zero (step S36), and then proceeds to step S14 so as to add 1 (increment) to the integer s (step S14). Subsequently, the microcomputer 70 compares the actual impedance and the target Ri corrected in S34, to thereby perform the heater control (Ri constant control) processing (step S16). After that, the microcomputer 70 ends the processing of detecting the degree of deterioration of the cell 2, and returns to the main routine.

Meanwhile, in the case where the result of the determination in step S26 is "No", the microcomputer 70 proceeds to step S36 without correcting the target Ri (without performing steps S28 to S34). As a result, the microcomputer 70 does not detect the degree of deterioration of the cell 2 when the air-fuel ratio (λ) is on the lean side, on which side the value of ΔVri becomes unstable as discussed below. Therefore, the target Ri is prevented from being corrected improperly.

Figure 6B:
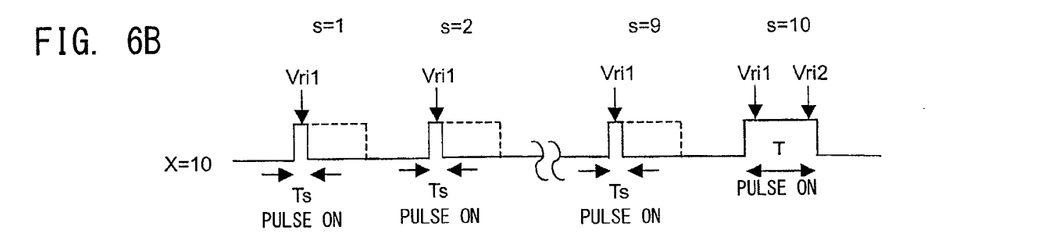

Meanwhile, in the case where the deterioration detection timing coefficient x is equal to or greater than 2, the result of the determination in step S10 becomes "No" in some cases. In such a case, as shown in FIG. 6B, the pulse width of the single pulse voltage becomes equal to an energization time Ts shorter than the time T. The pulse width (time Ts) is shorter than the second time t2. Therefore, in the case where the pulse width is equal to the time Ts, the impedance signal Vri2 is not obtained, and calculation of the difference ΔVri and detection of the degree of deterioration are not performed. Next, the flowchart of FIGS. 5A and 5B will be described for the case shown in FIG. 6B in which the deterioration detection timing coefficient x is 10.

First, in the processing (subroutine) performed for the first time for calculating the degree of deterioration, steps S2 to S8 of FIG. 5A are performed. Since the initial value of s is 1, the result of the determination in step S10 becomes "No". In such a case, the microcomputer 70 stops application of the single pulse voltage (pulse OFF) in step S12, and then proceeds to step S14 so as to add 1 (increment) to the integer s. As a result, the pulse width of the single pulse voltage becomes Ts (<T).

Next, the microcomputer 70 performs the heater control (Ri constant control) while using the target Ri (step S16), and ends the processing for detecting the degree of deterioration of the cell 2. This corresponds to the left end pulse of FIG. 6B, and the pulse width is equal to time Ts. Therefore, only the impedance signal Vri1 is obtained for calculation of Ri, and neither calculation of the difference ΔVri nor detection of the degree of deterioration is performed.

In the subroutine performed for the second time, since s=2, the result of the determination in step S10, performed after steps S2 to S8, becomes "No". Therefore, the microcomputer 70 ends the processing in step S16. Since the value of s is still less than 10 when step S10 is performed during the ninth time execution of the subroutine, the result of the determination in step S10 again becomes "No". That is, all the pulse widths of nine pulses (a pulse in the left end period (s=1) of FIG. 6B to a pulse in a period corresponding to s=9 (FIG. 6 shows only three of the shorter pulses) become Ts (<T). Therefore, only the impedance signal Vri1 is obtained for calculation of Ri, and none of calculation of the difference ΔVri and detection of the degree of deterioration is performed.

However, since 1 (increment) is added to s in step S14 every time the subroutine is performed, the value of s becomes 10 after the end of the ninth time execution of subroutine.

Subsequently, when the subroutine is performed for the tenth time, since s=10, the result of the determination in step S10 becomes "Yes", and the microcomputer 70 proceeds to steps S20 to S36. In this case, the pulse width of the single pulse voltage becomes equal to the time T, both the impedance signals Vri1 and Vri2 are obtained and the difference ΔVri is calculated, and the degree of deterioration of the cell 2 is detected (see the pulse in the right end of FIG. 6B corresponding to s=10).

As described above, the deterioration detection timing coefficient x defines the timing of detection of the difference ΔVri. When x=1, the difference ΔVri is detected every time the impedance Ri is detected. When x=n, the difference ΔVri is detected every time the impedance Ri is detected n times.

Accordingly, by setting the deterioration detection timing coefficient x, it becomes possible to detect the difference ΔVri every time the impedance Ri is detected in order to increase the number of times of detection of the degree of deterioration to thereby improve the detection accuracy, or to decrease the number of times that the difference ΔVri (the degree of deterioration) is detected, to thereby reduce the processing load of the microcomputer 70. That is, the detection timing of the difference ΔVri (the degree of deterioration) can be set properly in accordance with the environment in which the gas sensor 10 is used, the performance of the ECU 100, or the like.

Notably, upon application of the single pulse voltage, a charge is stored in the cell 2 which affects properties of the solid electrolyte body. Therefore, preferably, after the cell 2 is left as it is for a certain period of time after stopping the single pulse voltage, the next supply of the single pulse voltage is performed. Thus, the charge stored in the cell 2 is eliminated, whereby the cell 2 is returned to a normal state.

Particularly, the next single pulse voltage is preferably applied after elapse of a waiting time from the previous application of the single pulse voltage, the waiting time being equal to or greater than 10 times the constant energization time T. For example, in the example shown in FIGS. 2 and 3, the constant energization time T is 5 ms, and the interval between the single pulse voltages is 500 ms. Therefore, the waiting time (500-5 (ms)) is set to 99 times the constant energization time T.

Figure 7:
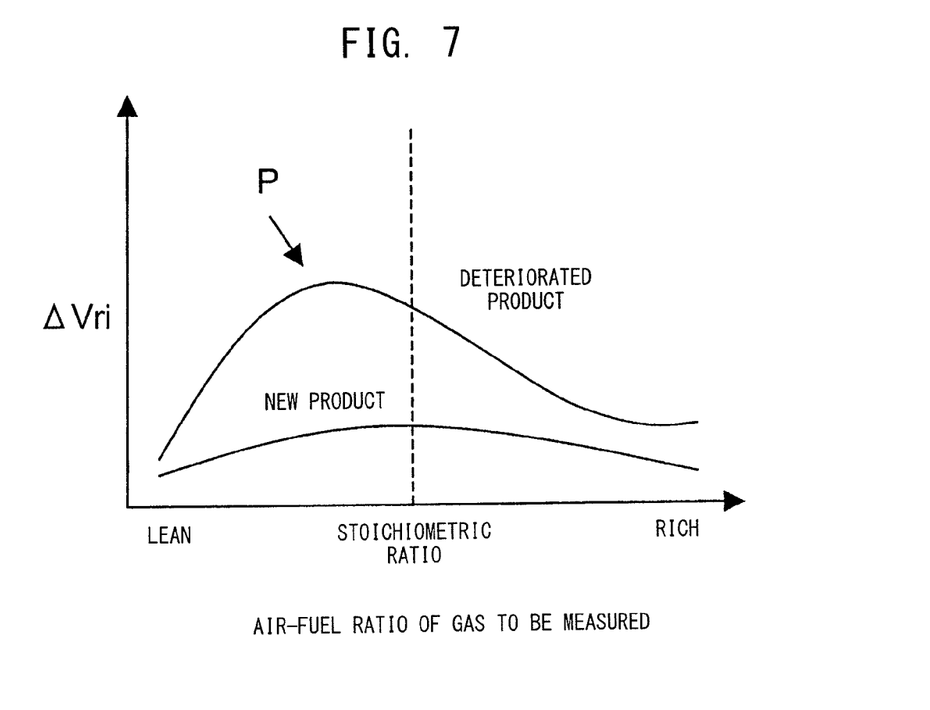
FIG. 7 is a graph showing the relationship between the air-fuel-ratio of a gas to be measured and $\Delta Vri$.

Also, as shown in FIG. 7, in the case of a deteriorated gas sensor (a gas sensor 10 used in travel of 60,000 km in total), the value of ΔVri reaches its peak P at a certain air-fuel ratio λ on the lean side, and greatly changes and becomes unstable in the certain air-fuel ratio region in which the value of the difference ΔVri is not the peak P. That is, if the degree of deterioration of the cell 2 is detected when the air-fuel ratio λ is on the lean side where the value of the difference ΔVri is unstable, the detection accuracy of the degree of deterioration may become lower.

In order to overcome such a drawback, when the air-fuel ratio of the gas to be measured (exhaust gas) surrounding the gas sensor 10 assumes a specific value (in the example of FIGS. 5A and 5B, in step S26, the air-fuel ratio is determined to be on the rich side), the degree of deterioration of the cell 2 is selectively detected. Thus, a situation can be avoided where the degree of deterioration of the cell 2 is detected when the air-fuel ratio is in an air-fuel ratio region (lean region) in which the value of the difference ΔVri is unstable.

The present invention is not limited to the above-described embodiment, and encompasses various modifications and equivalents which fall within the spirit and scope of the claims appended hereto. For example, in the above-described embodiment, the cell 2 is a λ (lambda) sensor (an oxygen sensor which detects λ and outputs a two-value signal representing whether the air-fuel ratio is on the rich side or the lean side). However, the type of sensor is not limited thereto insofar as the sensor employs a solid electrolyte body having oxygen-ion-conductivity. For example, the present invention can be applied to a full-range air-fuel ratio sensor or an $NO_X$ sensor.

In the above-described embodiment, the degree of deterioration is detected, and the target Ri is corrected (compensated) on the basis thereof. However, the present invention is not limited thereto. For example, the embodiment may be modified such that the output value of the gas sensor is directly corrected in accordance with the degree of deterioration of the cell. Also, the embodiment may be modified such that, when the degree of deterioration (the difference ΔVri) exceeds a predetermined threshold value, the gas sensor is determined to be broken.

In the above-described embodiment, the gas sensor control apparatus of the present invention is incorporated in the ECU 100. However, the gas sensor control apparatus may be provided separately from the ECU 100. That is, a separate gas sensor control apparatus in which the output detection circuit 20, the heater control circuit 60, and a microcomputer capable of executing the above-described heater control processing and the above-described processing of detecting the degree of deterioration are mounted on a circuit board may be provided between the gas sensor 10 and the ECU 100.

This application is based on Japanese Patent Application No. 2010-265173 filed Nov. 29, 2010, the disclosure of which is incorporated herein by reference in its entirety.

What is claimed is:

1. A control apparatus for a gas sensor which includes a cell composed of an oxygen-ion-conductive solid electrolyte body and a pair of electrodes provided thereon and which generates a sensor output corresponding to concentration of a specific gas, the control apparatus comprising:
   a voltage applicator that applies a single pulse voltage to the cell over a constant energization time;
   a first-output-value obtainer that obtains a first output value from the cell when a first time shorter than the constant energization time has elapsed after a start of application of the single pulse voltage;
   a second-output-value obtainer that obtains a second output value from the cell when a second time shorter than the constant energization time but longer than the first time has elapsed after the start of application of the single pulse voltage; and
   a deterioration-degree detector that detects a degree of deterioration of the cell based on a difference between the second output value and the first output value.

2. The control apparatus for a gas sensor according to claim 1, wherein the second time is longer than two times the first time.

3. The control apparatus for a gas sensor according to claim 1, wherein the voltage applicator again applies the single pulse voltage after a waiting time equal to or longer than 10 times the constant energization time has elapsed after the previous application of the single pulse voltage.

4. The control apparatus for a gas sensor according to claim 1, wherein
the gas sensor is placed in a passage through which exhaust gas from an internal combustion engine flows;
the control apparatus comprises a determiner that determines an air-fuel ratio of the exhaust gas based on the sensor output; and
the deterioration-degree detector detects the degree of deterioration when the air-fuel ratio determined by the determiner is a specific air-fuel ratio.

5. The control apparatus for a gas sensor according to claim 4, wherein
the determiner determines, based on the sensor output, whether the air-fuel ratio of the exhaust gas is on a rich side or a lean side; and
the deterioration-degree detector detects the degree of deterioration when the specific air-fuel ratio determined by the determiner is an air-fuel ratio on the rich side.

6. The control apparatus for a gas sensor according to claim 1, wherein
the gas sensor includes a heater for heating the cell; and
the control apparatus further comprises a heater controller that controls an amount of electric current supplied to the heater such that the cell assumes a target impedance, and a changer that changes the target impedance based on the degree of deterioration detected by the deterioration-degree detector.

7. A method for controlling a gas sensor which includes a cell composed of an oxygen-ion-conductive solid electrolyte body and a pair of electrodes provided thereon and which generates a sensor output corresponding to concentration of a specific gas, the method comprising:
applying a single pulse voltage to the cell over a constant energization time;
obtaining a first output value from the cell when a first time shorter than the constant energization time has elapsed after a start of application of the single pulse voltage;
obtaining a second output value from the cell when a second time shorter than the constant energization time but longer than the first time has elapsed after the start of application of the single pulse voltage; and
detecting a degree of deterioration of the cell based on a difference between the second output value and the first output value.

8. The method according to claim 7, wherein the second time is longer than two times the first time.

9. The method according to claim 7, further comprising again applying the single pulse voltage after a waiting time equal to or longer than 10 times the constant energization time has elapsed after the previous application of the single pulse voltage.

10. The method according to claim 7, wherein the gas sensor is placed in a passage through which exhaust gas from an internal combustion engine flows, and
the method further comprising:
determining an air-fuel ratio of the exhaust gas based on the sensor output; and
detecting the degree of deterioration when the determined air-fuel ratio is a specific air-fuel ratio.

11. The method according to claim 10, further comprising:
determining, based on the sensor output, whether the air-fuel ratio of the exhaust gas is on a rich side or a lean side; and
detecting the degree of deterioration when the specific air-fuel ratio determined by the determiner is an air-fuel ratio on the rich side.

12. The method according to claim 7, wherein the gas sensor includes a heater for heating the cell, and
the method further comprises:
controlling an amount of electric current supplied to the heater such that the cell assumes a target impedance; and
changing the target impedance based on the degree of deterioration detected by the deterioration-degree detector.

* * * * *